United States Patent
Park et al.

(10) Patent No.: US 9,775,752 B2
(45) Date of Patent: Oct. 3, 2017

(54) INDIVIDUALLY PACKAGED ABSORBENT ARTICLE

(75) Inventors: Hyung Woo Park, Gyeonggi-do (KR); Hyong Bom Kim, Gyeonggi-do (KR); Sung Su Kim, Gyeonggi-do (KR); Seong Dae Roh, Gyeonggi-do (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 227 days.

(21) Appl. No.: 14/364,132

(22) PCT Filed: Dec. 19, 2011

(86) PCT No.: PCT/KR2011/009795
§ 371 (c)(1),
(2), (4) Date: Jun. 10, 2014

(87) PCT Pub. No.: WO2013/094779
PCT Pub. Date: Jun. 27, 2013

(65) Prior Publication Data
US 2015/0018795 A1    Jan. 15, 2015

(51) Int. Cl.
*A61F 13/47*    (2006.01)
*A61F 13/56*    (2006.01)
*A61F 13/551*    (2006.01)
*A61F 13/476*    (2006.01)

(52) U.S. Cl.
CPC ...... *A61F 13/5514* (2013.01); *A61F 13/4704* (2013.01); *A61F 13/5616* (2013.01); *A61F 13/476* (2013.01)

(58) Field of Classification Search
CPC ............ A61F 13/55175; A61F 13/5518; A61F 2013/55195; A61F 13/5514; A61F 13/4704; A61F 13/5513; A61F 13/5611; A61F 13/5616; A61F 13/475; A61F 13/4751; A61F 13/4752; A61F 13/476
See application file for complete search history.

(56) References Cited

U.S. PATENT DOCUMENTS

| | | | |
|---|---|---|---|
| 4,285,343 | A | 8/1981 | McNair |
| 4,556,146 | A | 12/1985 | Swanson et al. |
| 4,589,876 | A | 5/1986 | Van Tilburg |
| 4,917,697 | A | 4/1990 | Osborn, III et al. |
| 5,181,610 | A | 1/1993 | Quick et al. |

(Continued)

FOREIGN PATENT DOCUMENTS

| | | |
|---|---|---|
| EP | 0 527 171 B1 | 2/1993 |
| EP | 0 637 234 B1 | 3/1995 |

(Continued)

OTHER PUBLICATIONS

Search Report and Written opinion for PCT/KR2011/009597, Aug. 22, 2012, 3 pages.

*Primary Examiner* — Peter S Vasat
(74) *Attorney, Agent, or Firm* — Kimberly-Clark Worldwide, Inc.

(57) ABSTRACT

The present application discloses and claims an individually packaged, absorbent article of enhanced length, and including at least two sets of wings, which article is folded into a compact package form, and which package in being unfolded by a consumer, results in less operation steps by the consumer for donning of the article, and for disposal of the package.

23 Claims, 7 Drawing Sheets (56) References Cited

U.S. PATENT DOCUMENTS

| | | | |
|---|---|---|---|
| 5,683,377 A | 11/1997 | Mizutani | |
| 6,074,376 A | 6/2000 | Mills | |
| 6,168,582 B1* | 1/2001 | Hasegawa | A61F 13/5514 206/438 |
| 6,502,695 B1 | 1/2003 | Kim et al. | |
| 8,052,664 B2 | 11/2011 | Shimizu et al. | |
| 8,491,553 B2 | 7/2013 | Nomoto et al. | |
| 2002/0156448 A1* | 10/2002 | Steger | A61F 13/84 604/385.06 |
| 2004/0243087 A1* | 12/2004 | Kinoshita | A61F 13/4753 604/385.04 |
| 2008/0269708 A1 | 10/2008 | Caracci et al. | |

FOREIGN PATENT DOCUMENTS

| | | | |
|---|---|---|---|
| EP | 0 865 264 B1 | 9/1998 | |
| EP | 1 142 546 B1 | 10/2001 | |
| EP | 1 327 429 B1 | 7/2003 | |
| EP | 1 762 208 A2 | 3/2007 | |
| EP | 1 762 208 A3 | 3/2007 | |
| JP | WO 2010035648 A1 * | 4/2010 | A61F 13/5514 |
| JP | WO 2010109995 A1 * | 9/2010 | A61F 13/5514 |
| WO | WO 9820823 A2 | 5/1998 | |
| WO | WO 9820823 A3 | 5/1998 | |
| WO | WO 9825561 A1 | 6/1998 | |
| WO | WO 9842285 A1 | 10/1998 | |
| WO | WO 9842287 A1 | 10/1998 | |
| WO | WO 9842289 A1 | 10/1998 | |
| WO | WO 9853781 A1 | 12/1998 | |
| WO | WO 9853782 A1 | 12/1998 | |
| WO | WO 9925285 A1 | 5/1999 | |
| WO | WO 9955268 A1 | 11/1999 | |
| WO | WO 2007041210 A1 | 4/2007 | |

* cited by examiner

INDIVIDUALLY PACKAGED ABSORBENT ARTICLE

CROSS REFERENCE TO RELATED APPLICATION

This application is the national stage entry of International Patent Application No. PCT/KR2011/009795 having a filing date of Dec. 19, 2011, the entire contents of which is incorporated herein by reference.

TECHNICAL FIELD

The present invention relates to packaged absorbent articles. More particularly, it relates to absorbent personal care articles having foldable wings or flaps that can be employed to properly position and attach the absorbent articles to undergarments or other articles of clothing.

BACKGROUND ART

Absorbent articles, such as feminine hygienic articles (sanitary pads and panty liners), and adult incontinence pads are often worn in the crotch area of a user's undergarments. Prior to use, these types of articles are frequently individually wrapped in a compact package for ease of handling and discreteness. These articles are designed to provide some sense of normalcy in a user's daily activities by absorbing and retaining uncontrolled body excretions and avoiding embarrassing staining of garments. To accommodate the needs of many different types of consumers, various shapes and sizes of such absorbent articles have been developed. Features have been introduced to enable use of these articles with relative ease. In this regard, some of these absorbent articles have included wings or flaps (sometimes also named tabs) to enable the articles to be firmly secured to the garment facing side of a user's undergarments. These flaps or wings may either be integral extensions of layers of the main body of an absorbent article, or alternatively, may be separate structural attachments to the main body of an absorbent article. The wings are often provided with a garment attachment means or fastener, typically in the form of an adhesive patch, for affixing them in place to the underside of a user's undergarments in the crotch region. It has been found that the wings provide both a protective barrier at the lengthwise edges of the article, to alleviate exudate leakage, and also a means for maintaining the product in a stable position during use. An example of such absorbent articles with wings, can be found in U.S. Pat. No. 4,285,343 to McNair, U.S. Pat. No. 4,589,876 to Van Tilberg, EP 0637234 to 3M Company and U.S. Pat. No. 6,502,695 to Kim, each of which is hereby incorporated by reference thereto in its entirety.

The wing adhesive patches or other types of fastener systems (such as a combination of mechanical and adhesive systems, or solely mechanical systems) employed by such articles are often covered by adhesive release sheets (fastener covers) in the case of adhesive patch systems. The release sheets are typically in the form of coated papers or films, such that the adhesive components are not exposed to the environment prior to use, and can be easily separated from the release sheet at the time of use. The release sheets may be individual sheets separately attached to each wing adhesive patch, or alternatively "bridge"-like sheets which cover multiple wings with one release sheet. If the sheets are separate individual sheets, they may be discrete release sheets, each positioned on one wing adhesive patch, or lightly adhesively attached to each other for ease of removal, one at a time, in order to avoid inadvertent sticking of adhesive patches to undesired locations. Alternatively, the single bridge-like release sheet may be a rectangular sheet or a rectangular sheet which includes a perforation for later separation. The covered wings may be folded over either the top side or bottom side of the article during manufacture, and pre-use storage of the article. In such case, if the wings are folded over the top side of the article, the topsheet of the wing would come in contact with the topsheet of the article, and the backsheet of the wing would be situated facing the wing release sheet(s). In the case of purely mechanical wing fasteners (hook and loop devices), such wings are typically also folded over either the top side or bottom side of the article during manufacture and pre-use storage of the article. Such mechanical fasteners on opposing wings, are often adhered directly to each other in pre-use storage condition.

The absorbent articles may also include additional fastener systems on the underside of the central main body of the article, so as to provide either adhesive or other mechanisms for securing the longitudinal central axis of the article to the longitudinal axis of the crotch region (user facing side) of a user's undergarments when in use. Such additional fastener system frequently consists of a series of adhesive patches (also known as garment adhesive patches) along the longitudinal axis of the garment facing backsheet of the article. The garment adhesive patches may be covered by one or more separate release sheets or fastener covers (as with the wing adhesive patches) and are typically comprised of the same releasable sheet materials as the wing adhesive release sheet(s). If the garment adhesive patches are present and covered with separate release sheets, the release sheets each need to be removed by the consumer in a separate step prior to adhering the article to his/her undergarment. Essentially, the consumer needs to remove the one or more wing adhesive release sheets and then remove the one or more garment adhesive release sheets prior to donning the article.

Alternatively, the garment adhesive release sheets may be adhesively attached via several patches of adhesive, to the inside surface of an outer pouch/wrapper, if the article is stored in an individual pouch/package. Typically in this configuration, the adhesive strength of these patches is stronger than that of the garment adhesive patches which hold the article to the release sheet. In this instance, when a user removes the article from its outer pouch or wrapper, the release sheet remains with the wrapper for disposal, but the article is free to be removed from the release sheet. The consumer would then only need to separately remove the wing adhesive release sheets prior to product application. Alternatively, the garment adhesive patches are directly covered by the inside surface of the individual storage pouch/wrapper (rather than a separate release sheet) during the manufacturing and folding operation, such as described in U.S. Pat. No. 4,556,146 to Swanson and U.S. Pat. No. 5,181,610 to Quick which are hereby incorporated by reference in their entirety. In such instances, the individual pouch is made from a film or film laminate which includes a release coating, such as a silicone coating, for ease of peel of the article from the outer pouch material prior to use.

Depending on the type and size of absorbent article, such articles may have one or more sets of wings or flaps to help stabilize the article in use and to prevent leakage. For example, for sanitary pads which are typically used daily by women during their monthly menstrual cycles, an article with one centrally positioned set of wings (along the longitudinal axis) may be preferred. For sanitary pads which are to be used over night by women to capture menstrual exudates during sleep, larger pads with two or more sets of wings may be preferred. Such larger pads provide a sense of security for women, knowing that they will not need to arise to check or change their pads until morning. Such pads typically include a central or more frontwardly positioned wing set for adhering to the underside of the user's undergarments, and a rearwardly positioned wing set to adhere to the inside of a user's undergarments in the buttocks region. Similarly, for adult incontinence pads, physically larger and higher absorbent capacity pads may be desired, also accompanied by multiple sets of leakage preventing and fastening wings.

In absorbent articles with wings, various configurations of adhesive release sheets are often described for use to cover the wing adhesive patches and garment adhesive patches, because of the inconvenience of removing multiple pieces of paper during the product application process. For example, in early product configurations, the consumer removed the article from the wrapper and then separately removed a separate garment adhesive release sheet and wing adhesive release sheet(s) prior to donning and use of the article. In this configuration, the absorbent article is not attached to the individual storage pouch in any way. Such operation required between two and three separate action steps by the consumer prior to application of the article to a user's undergarments (donning), and left the consumer with multiple pieces of material for separate disposal (as in the pouch material, and two or more release sheet materials, depending on whether the wings each had separate wing adhesive release sheets).

In later alternative designs, also described in the literature, the article design includes a garment adhesive release sheet itself bonded or not, to the outer pouch, and a single bridge-like wing adhesive release sheet not bonded to the outer pouch. Such package requires from one to two separate action steps on the part of the consumer, prior to applying the product to their undergarment. In still another alternative configuration, the garment adhesive release sheet(s) and wing adhesive release sheet(s) are instead all additionally affixed to a surface portion of the outer pouch material and are removed in one operation upon removal of the article from the pouch. In such a configuration, which is often preferred by a consumer, essentially one piece of waste material is generated for a single disposal. The adhesive strengths of the adhesive patches connecting release sheets to the pouch/wrapper, are each stronger than the strengths connecting the article to the release sheets, as typically the latter adhesive is of a light pressure sensitive adhesive variety, and the former is of a more permanent, cured non-tacky adhesive variety. Further, the consumer does not have to manipulate multiple pieces of release sheets during the article application, which could lead to adhesive patches being inadvertently stuck to either other portions of the article itself, or unintended areas of the consumer undergarment/outergarments. Such inadvertent adhesion of the article to unintended locations leads to consumer frustration. Examples of bridge-like release sheets can be seen in EP0527171 to Davis, EP 1 327 429 to Kashiwaga, and EP 1 142 546 to Luizzi. Such bridge-like release sheets may require multiple steps of removal prior to use. Structural configurations for one step removal of release sheets from a single wing set-containing article are described for example, in EP 865264 to Hansson, U.S. Pat. No. 6,074,376 to Mills, and U.S. Pat. No. 5,683,377 to Mizutani and U.S. Pat. No. 6,502,695 to Kim.

So as to accommodate the structural challenges presented by multiple wing set-containing articles, numerous other release sheet configurations have been described in the patent art for removal in one or multiple steps. Some designs for example, are described in WO98/20,823 to Snauwaert, WO 98/25,561, WO 98/53,781 and WO 98/53,782 to Hasegawa, WO 99/25,285 and WO 99/55,268 to Nishida, and WO 98/42,285, WO 98/42,287, and WO 98/42,289 to Shimizu.

Despite each of these configurations there is still a need for an individually packaged absorbent article with efficient adhesive release sheet designs for long, multiple wing set-containing articles, and which still provides the consumer with a compacted package that offers the capability for removal of all release sheets in one operation, such that the consumer has only one piece of material waste to dispose of. The need is especially evident in longer absorbent products which may be used for high absorbency applications or overnight applications.

As indicated, during manufacture, the absorbent articles are often folded along one or multiple fold lines into a more compact configuration, and then placed into the individual storage pouch, package or wrapper, until use. The individual pouch or package protects the article from soiling and contamination before use and allows the user to carry one or multiple absorbent articles in a purse or pocket for later use without damage. Such pouch also provides a somewhat inconspicuous appearance to the absorbent article, such that a casual observer would not recognize the article for what it actually is, thereby sparing the user from potential embarrassment. A folded article in an individual pouch has therefore become a desirable consumer feature for these types of products. However, it has often been challenging to fold a long and high absorbent capacity article into a compact package that still offers the consumer advantages of one or few product application/donning/disposal steps. There is therefore a need for a compact individual package for long absorbent products with efficient placement of adhesive release sheets.

In the absorbent article field, it has also been desirable to include elastic components along an article's longitudinal side edges so as to promote a closer fit of the article to the consumer's body in use. Unfortunately, the folding of such articles for packaging often interferes with the long term performance of such elastic components, when the article is ultimately removed from the packaging and used. It has been found that the fold lines can deform elastic components such that their performance is impacted over time. There is therefore a need for a design for an individual package for a folded article, which allows for efficient removal of adhesive release sheets in one operation, and which also does not negatively impact the elastic performance of an article's elastic components during use.

DISCLOSURE OF INVENTION

Technical Problem

The present invention is therefore also directed to a folded, long absorbent article and individual package design, which allows for the efficient removal of adhesive release sheets from multiple wing sets, and which design does not negatively impact the elastic performance of articles containing such elastic components. The present invention can be used in conjunction with a variety of personal care absorbent articles including, but not limited to, diapers, training pants, incontinence articles, and feminine hygiene articles such as sanitary napkins and panty liners.

Solution to Problem

Objects and advantages of the invention are set forth below in the following description, or may be learned through practice of the invention.

In one embodiment of the invention an individually packaged absorbent article includes an absorbent article extending in a longitudinal direction and comprising a main body portion having a pair of longitudinal side edges, a pair of end edges, including a forward end edge and a rearward end edge, a garment facing surface provided with a main body garment fastener and a main body garment fastener cover, and a body facing surface, wherein the garment facing surface of the main body portion may be placed in a wearer's undergarment. The absorbent article includes a pair of forwardly positioned wings joined to the main body portion and extending laterally outward beyond the longitudinal side edges of the main body portion. A garment facing surface of each of the forwardly positioned wings includes a forwardly positioned wing fastener, and the forwardly positioned wings are folded over the body facing surface of the main body portion to expose the forwardly positioned wing fasteners. The main body portion further includes a pair of rearwardly positioned wings joined to the main body portion at a position closer to the rearward end edge than the forwardly positioned pair of wings, and extending laterally outward beyond the longitudinal side edges of the main body portion. A garment facing surface of each of the rearwardly positioned pair of wings includes at least one rearwardly positioned wing fastener, and the rearwardly positioned pair of wings is folded over the body facing surface of the main body portion to expose the rearwardly positioned wing fasteners. A wrapper for the absorbent article is included as well, with the wrapper including a main wrapper sheet, a pair of forwardly positioned wing fastener covers, and a pair of rearwardly positioned wing fastener covers. The main wrapper sheet includes a pair of longitudinal side portions, a pair of end portions, an article facing surface and an outer surface. The main wrapper sheet includes at least three fold lines and four faces divided by the three fold lines. The four faces each include an article-oriented face and an article opposing face. The four faces include a first face onto which the article rearward end edge extends, a second face onto which at least a portion of the folded rearwardly positioned wings and one or more of the rearwardly positioned wing fasteners are situated, a third face onto which the folded forwardly positioned wings are situated, and a fourth face onto which the forward end edge of the article is situated. The fold lines include a first fold line extending between the first face and the second face, the second fold line extending between the second face and the third face, and the third fold line extending between the third face and the fourth face. The pair of forwardly positioned wing fastener covers are releasably adhered to each other, with each of the pair of forwardly positioned wing fastener covers including a pair of longitudinal side portions, a pair of end portions, a releasable surface facing the wing fasteners of the forwardly positioned wings, and an opposing surface. The pair of forwardly positioned wing fastener covers extend only on the third face between the second and third fold lines, and the pair of forwardly positioned wing fastener covers are releasably affixed to the wing fasteners of the forwardly positioned wings. The pair of rearwardly positioned wing fastener covers are releasably adhered to each other, with each of the pair of rearwardly positioned wing fastener covers including a pair of longitudinal side portions, a pair of end portions, a releasable surface facing the pair of rearwardly positioned wing fasteners of the rearwardly positioned wings, and an opposing surface. The pair of rearwardly positioned wing fastener covers extend at least on the second face between the first and second fold lines. The pair of rearwardly positioned wing fastener covers are releasably affixed to the pair of rearwardly positioned wing fasteners of the pair of rearwardly positioned wings. The main wrapper sheet includes a first wing catch patch on the article-oriented face of the first face, for connecting to the pair of rearwardly positioned wing fastener covers when the article is in a folded configuration, and the main wrapper sheet further includes a second wing catch patch on the article-opposing face of the first face, for connecting to the forwardly positioned wing fastener covers when the article is in a folded configuration. The main wrapper sheet and the main body portion of the absorbent article are folded as a unit about the first, second and third fold lines so that the rearwardly positioned wing fastener covers are superposed with the first wing catch patch and the forwardly positioned wing fastener covers are superposed with the second wing catch patch, and all fastener covers are removed with the wrapper in one or more steps upon removal of the article from the wrapper.

In an alternative embodiment of the invention, the individually packaged absorbent article includes a main body fastener cover that is adhered to the wrapper rather than the article. In a further alternative embodiment of the invention, the individually packaged absorbent article includes rearwardly positioned wing fasteners of each rearwardly positioned wing in a number greater than one, which are positioned adjacent to each other in the article longitudinal direction, and further which are situated on each side of the first fold line. In still a further alternative embodiment of the invention, the individually packaged absorbent article includes rearwardly positioned wing fasteners on each rearwardly positioned wing in a number greater than one, and which are positioned adjacent to each other in the article transverse direction, and further which are situated on the same side of the first fold line within the second face. In still a further alternative embodiment of the invention, the individually packaged absorbent article includes rearwardly positioned wing fastener covers positioned solely on the second face. In a further alternative embodiment of the invention, the wing fastener covers are made of a single sheet, rather than multiple sheets. In still a further alternative embodiment of the invention, the absorbent article includes elastic features along its longitudinal edges. In still another alternative embodiment of the invention, the elastic side features are deadened in a region of said rearwardly positioned wing fasteners.

Those of ordinary skill in the art will better appreciate the features and aspects of such embodiments, and others, upon review of the specification.

BRIEF DESCRIPTION OF DRAWINGS

A full and enabling disclosure of the present invention is set forth more particularly in the remainder of the specification, including reference to the accompanying figures, in which:

FIG. 1a is a cross-section of the absorbent article of FIG. 1 taken along lines 1a-1a.

MODE FOR THE INVENTION

Reference will now be made in detail to present embodiments of the invention, one or more examples of which are illustrated in the accompanying drawings. Each example is provided by way of explanation of the invention and not a limitation of the invention. In fact, it will be apparent that modifications and variations can be made in the present invention without departing from the scope or spirit thereof. For instance, features illustrated or described as part of one embodiment may be used on another embodiment to yield a still further embodiment. Thus, it is intended that the present invention covers these and other such modifications and variations as come within the scope of the appended claims. It should be noted that like numbers may be used throughout the figures to identify like features.

Figure 1:
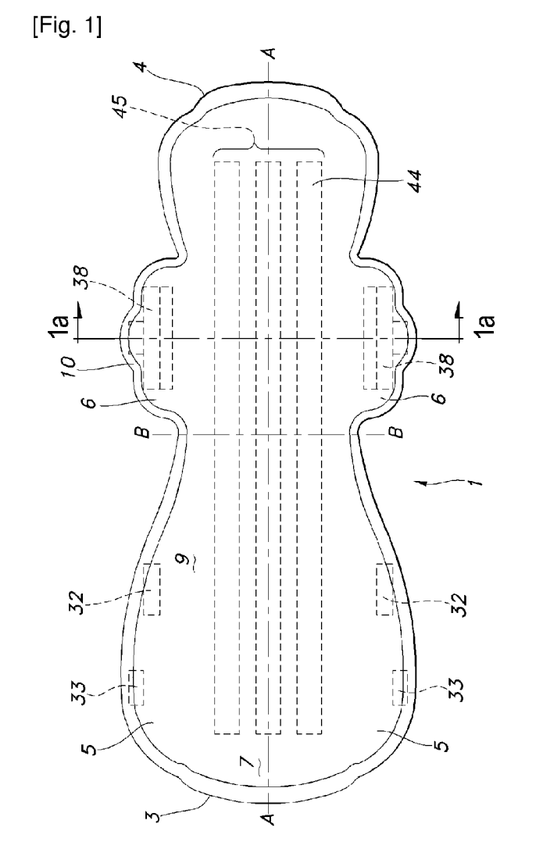
FIG. 1 is a top plan view of an absorbent article which may be used in conjunction with the individual package of the invention.
Figure 1A:
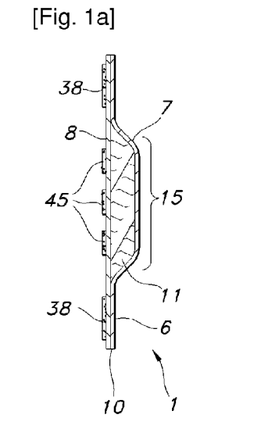
Figure 2:
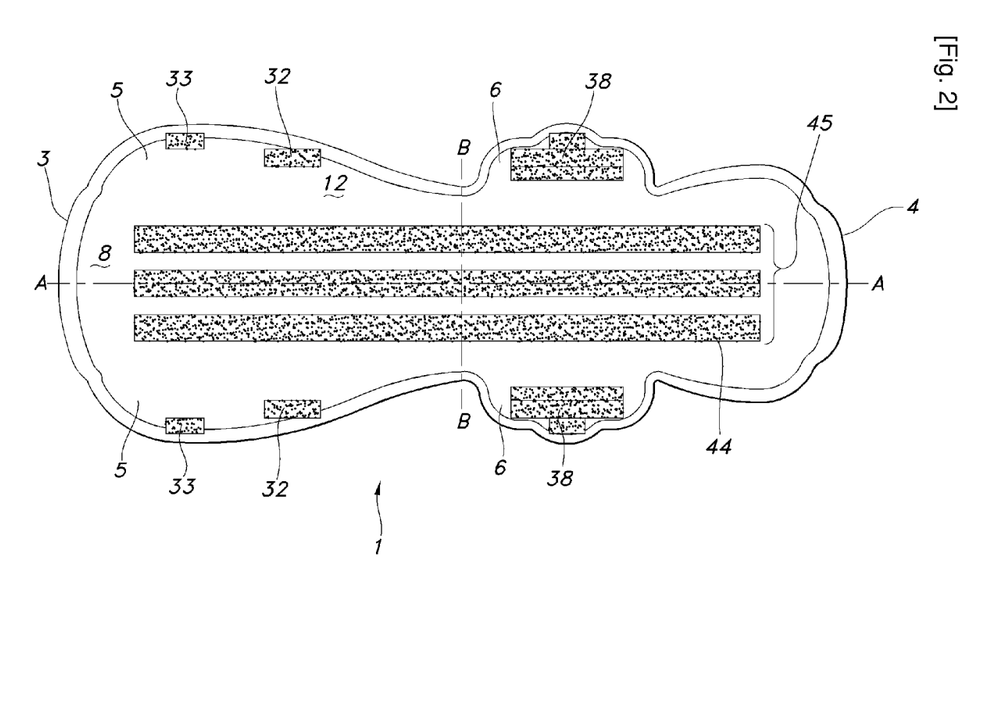
FIG. 2 is a bottom plan view of the absorbent article of FIG. 1.

As can be seen in FIGS. 1, 1a, and 2, an absorbent article 1, is illustrated in the form of a long overnight feminine hygienic pad, designed to be worn by a woman at least during the evening hours of her monthly menstrual cycle. The article is of extended length, especially when compared to traditional feminine napkins and pads, having a distinct longitudinal direction. In one embodiment, the article length (longest dimension from the article forward end to the rearward end) is between about 300 and 450 mm. In an alternative embodiment, the article length is between about 330 and 450 mm. In a further alternative embodiment, the article length is between about 400 and 450 mm.

Figure 3:
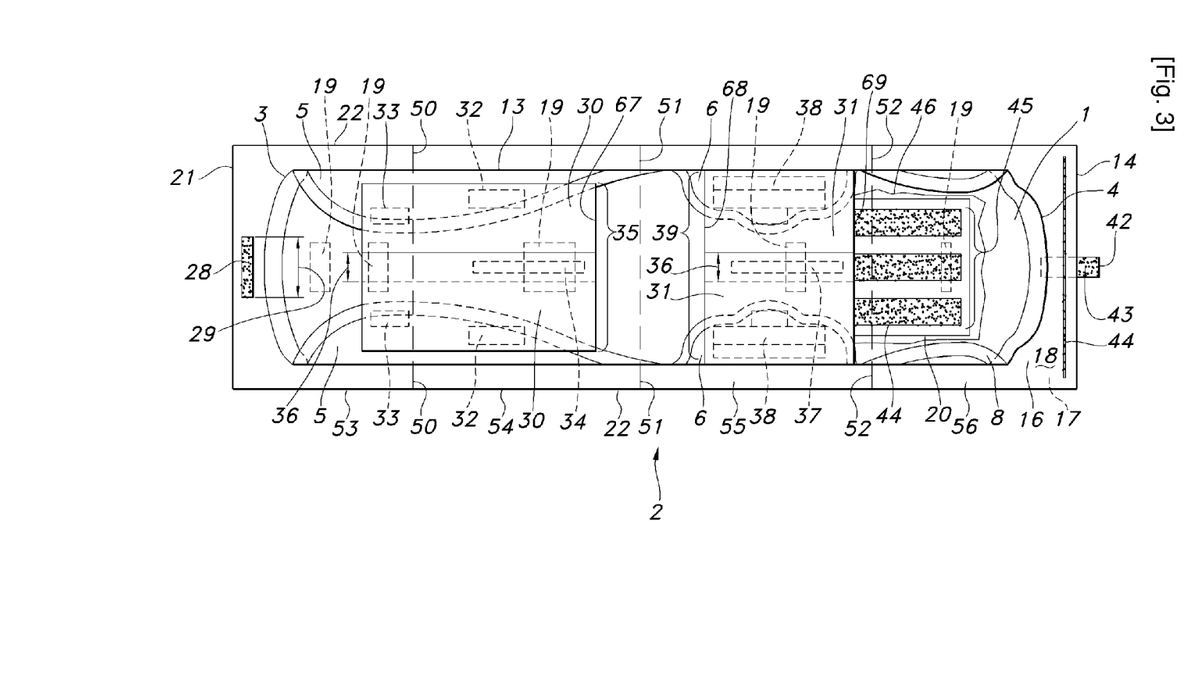
FIG. 3 is a top plan view of one embodiment of the individual article and pouch combination/package of the invention, including the absorbent article of FIG. 1 in a partially opened state.
Figure 3A:
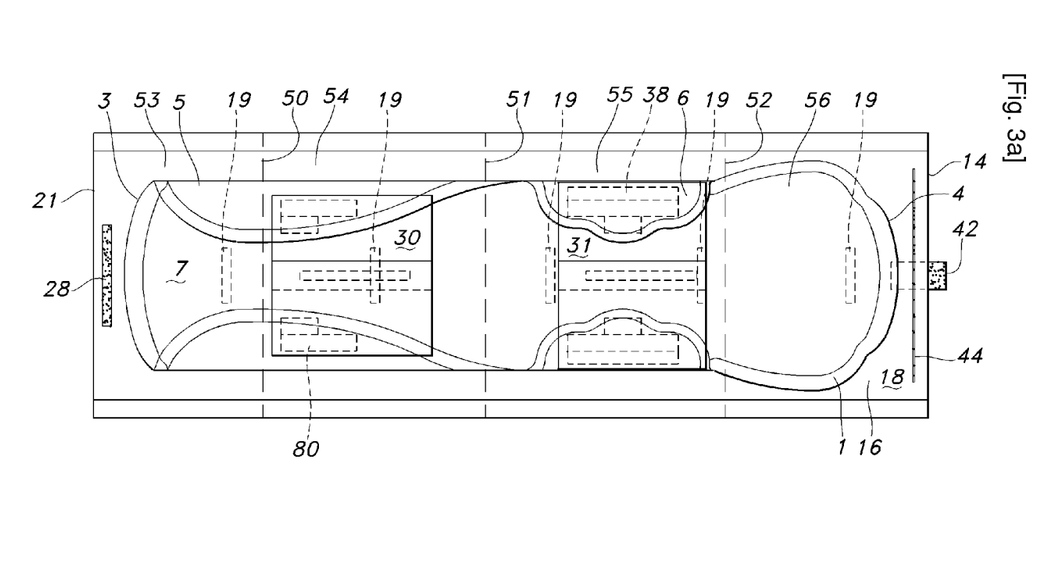
FIG. 3a is a top plan view of an alternative embodiment of the individual article and pouch combination/package of the invention, including an alternative embodiment of the absorbent article of FIG. 1 in a partially opened state.

A top plan view of an absorbent article is illustrated in FIGS. 1, 3 and 3a, showing a main body portion 15 (seen in FIG. 1a) having longitudinal side edges 13, a rearward end edge 3 and forward end edge 4. Off of the longitudinal side edges 13 of the absorbent article main body 15, are a laterally extended, rearwardly positioned set of wings 5, adjacent the rearward end edge 3, and a laterally extended, forwardly positioned set of wings 6 adjacent the forward end edge 4. The absorbent article includes a topsheet 7 for facing the user. A bottom plan view of the absorbent article is illustrated in FIG. 2, showing the backsheet 8 for facing a user's undergarments or garments. The absorbent article includes a central longitudinal axis A and a central transverse axis B. The fluid permeable topsheet 7 has a user facing surface 9, and the fluid impermeable backsheet 8 has a garment facing surface 12, with the topsheet 7 designed to contact the user's exposed body during use, and the backsheet 8 designed to contact the user's undergarments or garments during use. The topsheet 7 is desirable soft to the touch, and may be made for example, from a nonwoven or woven sheet, a perforated nonwoven sheet, a perforated film sheet, or a combination thereof (such as a laminate). The backsheet 8 may be made of any of various liquid impermeable materials, such as nonwovens, nonwoven laminates, polymeric films and combinations thereof. Desirably in one embodiment, the backsheet is breathable. The topsheet 7 is typically bonded to an underlying layer, such as the backsheet 8, most often at least along the peripheral edges 10 as can be seen in the cross-sectional view of FIG. 1a along line 1a-1a. Such bonding may be by traditional bonding techniques, for example by adhesive, thermal and ultrasonic bonding methods. The topsheet 7 and backsheet 8 sandwich at least one layer of absorbent material 11 which serves to capture exudates which pass through the topsheet 7 while the article is in use. Additional layers may also be positioned between the topsheet and the absorbent core, such as for example, surge layers, fluid transfer layers and fluid distribution layers. As topsheet, backsheet and absorbent core materials are well known in the art, further material description will not be provided herein.

At least one, and perhaps multiple patches of wing adhesive 32, 33, or other type of wing fasteners, are positioned upon the garment facing surface 12 of the backsheet 8, on the rearwardly positioned wings 5. In the illustration, two patches of wing adhesive are shown on each rearwardly positioned wing 5, so as to provide enhanced securement of the article in use. The wing adhesive patches are shown separated, but spaced adjacent to each other in the article longitudinal direction. Similarly, one or more patches of wing adhesive 38, or other type of wing fastener, are positioned upon the garment facing surface 12 of the backsheet 8 on the forwardly positioned wings 6. In the illustrated embodiment three patches of adhesive 38 are provided on the garment facing surface of the backsheet of the forwardly positioned wings 6, to provide enhanced securement of the article in use. These adhesive patches are shown spaced adjacent to each other along the article transverse direction. Prior to use and while stored in the package, the forwardly positioned and rearwardly positioned wings 5, 6 are folded over the topsheet 7 of the absorbent article. The wing adhesive patches are in one embodiment, pressure sensitive, resealable adhesive.

Three longitudinally directed stripes 44 of garment adhesive patches make up the main body garment fastener 45 of the main body portion, and are positioned on the garment facing surface 12 of the backsheet 8 symmetrically disposed along the longitudinal centerline/axis A of the absorbent article. Each of the adhesive patches are illustrated as traditional resealable, pressure sensitive adhesives known in the art, such as those described for example in U.S. Pat. No. 4,917,697 which is hereby incorporated by reference thereto in its entirety. It should be recognized that while each of the adhesive patches are shown in rectangular shapes, the sizes and shapes may be varied depending on product design, manufacturing, or consumer preferences. For example, the adhesive may run in the cross-machine or machine manufacturing direction, may entirely cover the backsheet surface 12, or only select portions of the backsheet surface.

As can be seen in FIG. 3, a top plan view of an individual package (pouch wrapper) and article combination 2 is illustrated with the absorbent article 1 of FIGS. 1, 1a, and 2 placed upon a pouch wrapper 16 such that the garment facing surface 12 of the absorbent article backsheet 8 is facing and in contact with, the inside surface, or article facing surface 18, of the pouch wrapper 16. The pouch wrapper 16 can be made of any known wrapper material in the art, such as for example a nonwoven, woven, cellulosic, film or other sheet material (such as a laminate combination of the foregoing materials), and includes an outer side 17 and an article facing side 18. This main wrapper sheet will eventually be folded to envelop the entire absorbent article 1. The main wrapper sheet is generally rectangular in configuration and includes a pair of longitudinal side portions 22, a pair of end portions 14, 21 an inner, article facing surface and an outer surface. In one particular embodiment, situated on the article facing side 18 (inner surface) of the wrapper 16 are a series of wrapper adhesive patches 19 for adhering the inside, article facing side 18 of the wrapper to the main body garment adhesive release sheet (or main body garment fastener cover) 20, shown in a cutaway opening 46 of FIG. 3. It should be recognized that while the single garment adhesive release sheet 20 is shown in a rectangular configuration having a pair of longitudinal side portions, a pair of end portions, an inner surface facing the article, and an outer surface facing the wrapper, it can be of any shape or number depending on design preferences. It should further be recognized that the wrapper adhesive patches 19 can be of any number, size or shape, and may be evenly spaced along the article longitudinal direction or unevenly spaced. Further examples of such wrapper adhesive patches can be seen in FIG. 3a. It should further be recognized that the cutaway opening 46 is presented solely for the ease of structural understanding by the reader, and no similar opening feature would be present in the actual individual package of the invention.

The garment adhesive release sheet 20 itself includes a wrapper facing surface, which is adhered to the adhesive patches 19 and an article facing surface, which is adhered to the garment fastener 45. It should be recognized that in an alternative embodiment, the adhesive patches 19 and garment adhesive release sheet 20 may be eliminated and the wrapper article facing surface 18 may be directly adhered to the garment fastener 45, rather than to an intermediary layer/release sheet 20. As previously discussed, in such a situation, it is desirable for the wrapper 16 to include a release coating at least on the article facing side 18 to ensure that the article can be easily peeled off from the individual garment adhesive patches 44 (of the garment fastener 45) during use. Alternatively, the garment adhesive release sheet 20 need not be adhered to the surface of the wrapper 16 at all. However, such a structure would by necessity result in more operation steps for the consumer in donning the article. It should be noted that in the embodiment illustrated, three portions of the absorbent article 1 are folded over the article topsheet 7, such that the backsheet portions 8, can be seen. However, only two of the folded portions (wings 5 and 6) include adhesive patches on the backsheet surface. A remaining folded portion, even more forward than the forwardly positioned wings 6, does not include adhesive patches. It is therefore contemplated that multiple additional folded portions can be included in absorbent articles of the invention, depending on product design preferences.

The adhesive strength of the wrapper adhesive patches 19 are in one embodiment, stronger than the adhesive strength of the garment fastener 45 so as to allow the garment adhesive release sheet 20 to stay with the wrapper 16 upon removal of the absorbent article 1 from the pouch wrapper 16. It should be understood that with respect to this application, adhesive strengths are described as being relative to each other, and that the term "adhesive strength" shall mean for the purposes of this application, the force required to separate two materials from each other at an adhesive or other bond site (such as at mechanical fastener site), that are held together solely via the adhesive or other bond. Any of a wide variety of adhesives or mechanical fasteners can be utilized in the individual packaged article of the invention, although releasable pressure sensitive adhesives are desirably used for adhesive patches that would come in eventual contact with a user's garment or that would serve to temporarily seal or reseal the opening of the pouch through a tab tape 42 or other line of adhesive 44, or further that would hold wing release sheets to each other. Non-releasable adhesive can desirably be used for adhesive patches that would hold the garment adhesive release sheet (s) 20 to the wrapper 16 or the wing adhesive release sheets 30, 31 to the wrapper 16 as will later be described. In an alternative embodiment, mechanical hook and loop fasteners may be used to hold garment adhesive release sheets or wing adhesive release sheets to the wrapper.

An optional tab tape 42 is positioned on the outer side 17 of the wrapper, and is permanently adhesively bonded to the outer side 17 surface. A portion of the tab tape 42 hangs over the edge of the pouch wrapper 16 and includes a tab tape adhesive patch of releasable/resealable pressure sensitive adhesive at its exposed end 43. In a further embodiment, a mechanical fastener may be used on the tab tape rather than an adhesive fastener. In a further alternative embodiment, a line of additional releasable/resealable pressure sensitive adhesive 44 is included adjacent the wrapper end 14 on the article facing side/surface 18 of the wrapper 16. The line of additional pressure sensitive adhesive 44 is situated between the article forward end 4 and the end of the wrapper along a transversely directed side edge 14. In one embodiment the wrapper includes a tab tape 42 and a line of additional pressure sensitive adhesive 44. In alternative embodiments, the wrapper includes only a tab tape, or alternatively, only a line of additional pressure sensitive adhesive. It should be recognized that the wrapper 16 includes transverse side edges 14 and 21 and includes two longitudinal directed side edges 22. On the side of the wrapper 16 longitudinally opposite the tab tape feature 42 (along the longitudinal direction of the pouch wrapper 16) is situated adjacent one transverse edge 21 a first wing catch patch, for example, an adhesive patch 28 on the article facing surface 18. Such first wing catch adhesive patch 28 may be a pressure sensitive adhesive or a more secure hot-melt type adhesive that is stronger in adhesive strength than the garment adhesive stripes 44 and wing adhesive patches previously described. Alternatively, such first wing catch adhesive patch 28 is a permanent adhesive that is not resealable or releasable once it is affixed to the wing release sheets 30 or release sheet combination 35. In still a further alternative embodiment, the wing catch patch can be a mechanical hook and loop fastener for catching either a hook or loop material of the wing release sheets.

A rearwardly positioned wing fastener cover, for example, wing adhesive release sheet, 30 is positioned over each of the rearwardly positioned wing adhesive patch sets 32, 33 of the rearwardly positioned wings 5, and is releasably secured thereto. Such wing adhesive release sheets 30 act to protect the wing adhesive patches from exposure to the environment. Each of the wing adhesive release sheets (or wing fastener covers) includes, in the illustrated rectangular embodiment, a pair of longitudinal side portions (along the length direction), a pair of end portions, a releasable surface facing the rearwardly positioned wing adhesive patch (or fastener) and an opposing surface, for facing the wrapper when in a folded configuration. Such adhesive release sheets 30 can in one embodiment, merely lie one atop the other in an overlapping configuration, or as shown, be adhesively adhered to each other in the overlapping region (releasably or permanently) via a rearwardly positioned wing release sheet adhesive patch 34. It has been found that the use of multiple release sheets 35 on the wing adhesive patches provides the manufacturer and consumer some flexibility in respectively manufacturing and opening the pouch. It should be understood though, that in an alternative embodiment one or more wing fastener covers (release sheets) may be used to cover each of the forwardly positioned or rearwardly positioned wing sets.

The first wing catch adhesive patch 28 desirably is of a length 29 that is longer than the overlapping portion of release sheets 36 in the transverse direction of the article, but is aligned with the overlapping portion in the longitudinal direction of the absorbent article, and both the overlapping portion 36 and first wing catch adhesive patch 28 are positioned symmetrically about the longitudinal axis A of the absorbent article. In an alternative embodiment, the length of the first wing catch adhesive patch 28 is equal or less in length than the overlapping portion 36 of the release sheets 30, but is aligned with the overlapping portion 36 along the longitudinal axis of the absorbent article. In a further alternative embodiment, a single wing release sheet (not shown) can be used such that the release sheet spans the two sets of wing adhesive patches. It should be recognized that such a configuration offers different functionality and requires different manufacturing steps than a configuration involving multiple release sheets. In a further alternative embodiment, the adhesive strength of the wing release sheet adhesive patch 34 if present, is greater than that of the strength of the wing adhesive patches 32, 33.

A forwardly positioned wing adhesive release sheet 31 is positioned over each of the forwardly positioned wing adhesive patches 38 of the forwardly positioned wings 6 and is releasably secured thereto. As with the previously described wing adhesive release sheets, such wing adhesive release sheets 31 act to protect the forwardly positioned wing adhesive patches 38 from exposure to the environment. Similarly, each of the forwardly positioned wing adhesive release sheets (or wing fastener covers) includes, in the illustrated rectangular embodiment, a pair of longitudinal side portions (along the length direction), a pair of end portions, a releasable surface facing the rearwardly positioned wing adhesive patch (or fastener) and an opposing surface for facing the wrapper when in a folded configuration. Similarly, such adhesive release sheets 31 can in one embodiment, merely lie one atop the other in a pair 39, or as shown, be adhesively adhered to each other in the overlapping region via a forwardly positioned wing release sheet adhesive patch 37. In an alternative embodiment, a single wing release sheet (not shown) can be used such that the release sheet spans the two sets of wing adhesive patches 38 on the forwardly positioned wings 6. In a further alternative embodiment, the adhesive strength of the wing release sheet adhesive patch if present, is greater than that of the strength of the wing adhesive patches. While the dimensions of the wing release sheets 30, 31 and the overlap of the wing release sheets 30 and 31 are shown to be equal, they need not be. It should be noted that examples of release sheets are described in U.S. Pat. No. 4,917,697.

On the pouch wrapper 16, are respectively positioned at least three fold lines, those being a first fold line 50, a second fold line 51, and a third fold line 52. The at least three fold lines create four faces on the wrapper, with each face having an article oriented face and an article opposing face separated by fold lines. The first face 53 is defined by the wrapper rearward edge 21, the first fold line 50 and the wrapper longitudinal edges 22. In this particular face, the article rearward end edge 3 is situated. It also includes thereon a portion of the article rearwardly positioned wings 5, and may include in one embodiment, some of the rearwardly positioned wing fasteners 33 (and covers 30). On this face 53 is situated thereon the first wing catch patch 28 (on the article facing side/surface 18 of the wrapper). Also on this face 53, but on the outer side 17, facing away from the article, is positioned thereon the second wing catch patch 57.

A second face 54 is defined by the first fold line 50, the second fold line 51 and the wrapper longitudinal side edges 22. The second face 54 of the wrapper, includes thereon at least a portion of the folded over rearwardly positioned wings 5, at least some of the rearwardly positioned wing fasteners 32 and covers 30. In one embodiment, the second face includes thereon all of the rearwardly positioned wing fasteners 80.

A third face 55, is defined by the second fold line 51, the third fold line 52 and the longitudinal side edges 22. It includes thereon the folded forwardly positioned wings 6, and the respective forwardly positioned wing fasteners 38 and covers 31.

A fourth face 56 of the wrapper is defined by the third fold line 52, the wrapper forward edge 14 and the longitudinal side edges 22. The fourth face 56 includes the article forward end edge 4.

The first fold line 50 is in one embodiment, situated between the two adhesive patches 32, 33 over the rearwardly positioned wings 5 in the direction along the article longitudinal axis/direction. The second fold line 51 is in one embodiment, situated between the forward edge 67 of the first set of wing release sheets 35 (on the rearwardly positioned wings) and the rearward edge 68 of the second set of wing release sheets 39 (on the forwardly positioned wings) along the article longitudinal axis/direction. The third fold line 52 is in one embodiment, situated between the second set of wing release sheets (the forwardly positioned wing release sheets) forward edge 69, and the wrapper forward edge 14 along the article longitudinal axis/direction.

As can be seen in FIG. 3a, an alternative embodiment of the individually packaged absorbent article is shown, in which the rearwardly positioned wing fastener covers (adhesive release sheets) are situated only on the second face 54 (face defined by the fold lines 50 and 51). In this embodiment, the adhesive patches 80 on the rearwardly positioned wings 5 are adjacent one another in the article transverse direction, and are situated on the same side of the first fold line 50, along the second face 54.

Figure 4:
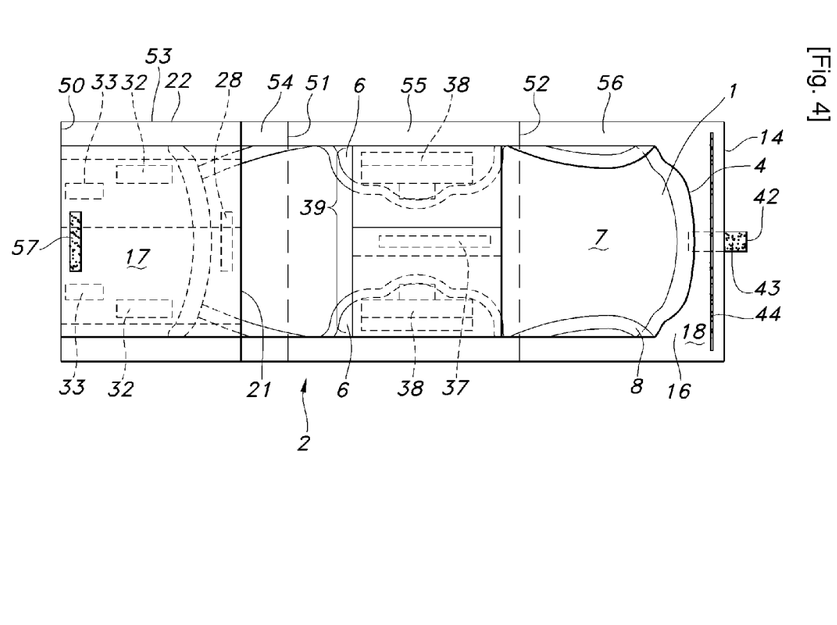
FIG. 4 is a top plan view of the individual article and pouch combination/package of FIG. 3 in a partially folded pouch configuration.

As can be seen in FIG. 4, which illustrates a top plan view of the individual absorbent article and pouch combination 2 of FIG. 3 in a partially folded configuration, a second wing catch patch 57, desirably an adhesive patch, is applied to the outer side 17 of the pouch wrapper 16 at a position adjacent a first fold line 50. The shape and dimensions of the second wing catch adhesive patch 57 are in one embodiment, the same as, or similar to those of the first wing catch adhesive patch 28. The second wing catch adhesive patch 57 is also aligned about the longitudinal axis A of the absorbent article with the first wing catch adhesive patch 28 but is situated on the opposite surface side of the same pouch face 53. As can be seen in phantom lines, when face 53 is folded about fold line 50 onto wrapper face 54, the first wing catch adhesive patch 28 is situated over and on top of (in contact with) the rearwardly positioned wing release sheets 30 thereby adhering to both their top surfaces (if the embodiment includes two release sheets 30). The first wing catch adhesive patch 28 catches either the single or multiple rearwardly positioned wing release sheet (s) such that upon opening and unfolding of the package by the consumer, the release sheet(s) 30 are pulled off of the wings 5 when the individually packaged article is opened and the absorbent article is removed from the pouch/wrapper. It should be recognized that each of the fold lines become at least a temporary wrapper edge during the manufacturing/folding process. The reverse unfolding process is later carried out by the consumer in the opening of the individually packaged article. In an alternative embodiment, it should be recognized that such wing catch patches may be of a mechanical hook and loop construction rather than adhesive. In a further alternative embodiment, it should be recognized that the wing catch patches 28, 57 may, instead of being positioned on the wrapper at first during manufacture, instead be positioned on the landing locations on the fastener covers (release sheets), which will eventually bring them into contact with the wrapper.

Figure 5:
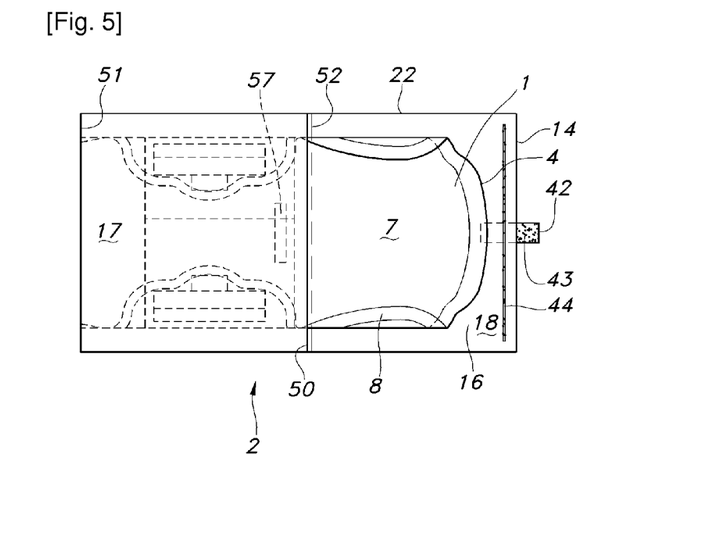
FIG. 5 is a top plan view of the individual article and pouch combination of FIG. 4 in a further folded pouch configuration.

As can be seen in FIG. 5, which illustrates a top plan view of the individual absorbent article and pouch combination 2 of FIG. 4 in a further folded configuration, the second wing catch adhesive patch 57 is situated on top of the forwardly positioned wing release sheets 31 when the wrapper face 54 is folded about fold line 51, placing it on top of/adjacent wrapper face 55. In this fashion, the second wing catch adhesive patch 57 lifts the adhesive release sheets 31 off of the forwardly positioned wing adhesive patches 38 during removal of the article 1 from the pouch 16 such that all adhesive release sheets are removed with the pouch wrapper, even though the article is long and includes two wing sets. During manufacture of the product, the adhesive patches 28 and 57 are desirably of the permanent hot melt type, and are affixed to the respective wing release sheets 30 and 31 at that time of initial manufacture and folding. Alternatively such adhesive can be of a pressure sensitive variety. However, the adhesive strength of the patches 28 and 57 is desirably higher than that of the wing adhesives holding the wing adhesive release sheets 30, 31 to the article.

Figure 6:
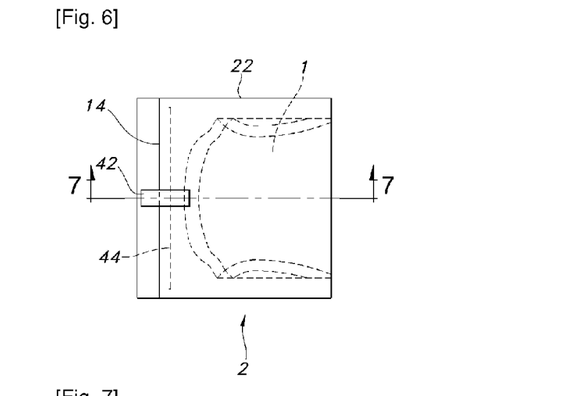
FIG. 6 is a top plan view of the individual article and pouch combination of FIG. 5 in a completely folded state.

As can be seen in FIG. 6, a top plan view of the completely folded individually packaged article of FIG. 5 is illustrated. The completely folded article and pouch combination 2 is created by folding the wrapper face 55 about fold line 52 onto wrapper face 56. The line of pressure sensitive adhesive 44 is adhered to the outer face 17 of the pouch wrapper on wrapper face 54. This line of adhesive offers, along with the tab tape 42, the opportunity for the consumer to releasably secure the pouch together, should it be opened and the consumer then choose for it to be resealed. As indicated, the adhesive patch 43 of the tab tape 42 is also adhered to the outer face 17 of the wrapper of face 54. The pouch is in one embodiment then frangibly sealed, such as by being thermally, ultrasonically or adhesively sealed about the pouch perimeter edges not having folds or sealing mechanisms as well (such as along longitudinal side edges 22), for completing the manufacture of the individually packaged article. Examples of frangible sealing methods are described in U.S. Pat. No. 4,556,146 to Swanson, which is hereby incorporated by reference thereto in its entirety.

Following manufacture of the individually packaged articles, numerous individually packaged articles are then themselves further packaged into an outer package, typically of a bag or carton construction.

In opening such an individually packaged article 2, the consumer would first lift up the tab tape 42 and separate the additional line of pressure sensitive adhesive from the pouch face. By unfolding the package, the wing adhesive release sheets would come off of the wings and adhere to the wrapper for eventual disposal by the consumer, thereby making the opening, donning and waste disposal process efficient.

Figure 7:
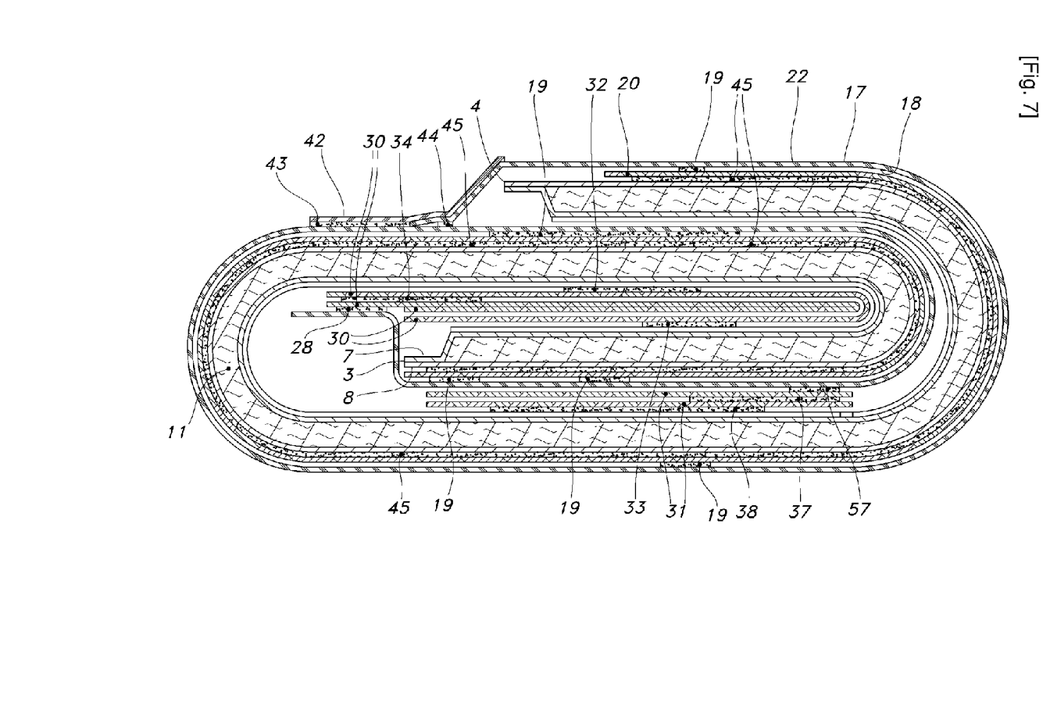
FIG. 7 is a cross-sectional view of FIG. 6 taken along line 7-7.

As can be seen in FIG. 7, which illustrates a cross-sectional view of the individually packaged absorbent article and wrapper combination of FIG. 6, taken along line 7-7, the garment adhesive release sheet 20, and wing adhesive release 30, 31 sheets are visible folded within the article 1, and pouch wrapper 16, such that as the wrapper is opened by a consumer, all of the adhesive release sheets are simultaneously removed with the wrapper for ease of disposal. This is accomplished for a long article, despite the article including numerous wing sets, and multiple folds which allow the article to be packaged into a relatively compact individual package.

During manufacture of the individually packaged absorbent article and pouch/wrapper combination 2, in one embodiment, the garment adhesive release sheet 20 is applied to the garment facing surface 12 of the backsheet 8 and the wings are folded over the topsheet 7 onto the topsheet surface 9. The wing adhesive release sheets are applied to the wing adhesive patches and the absorbent article is applied via the garment adhesive release sheet 20 onto the pouch wrapper 16 surface 18. Wing catch adhesive patches 28, 57 are applied to the outer side 17 of the pouch wrapper 16 and the article and pouch combination are subsequently folded such that a compact individually wrapped absorbent article package is produced, with the wing catch adhesive patches bonding permanently to the wing adhesive release sheets. The additional line of pressure sensitive adhesive 44 and tab tape adhesive patch 43 are contacted with the pouch face to seal the package along with frangible edge seals as desired. The design for the individually packaged absorbent article of the present invention provides a manufacturer the flexibility to remove either one of the wing catch patches 28, 57, thereby preventing all release sheets from coming off at the same time if such is desired by a particular consumer group.

Figure 8:
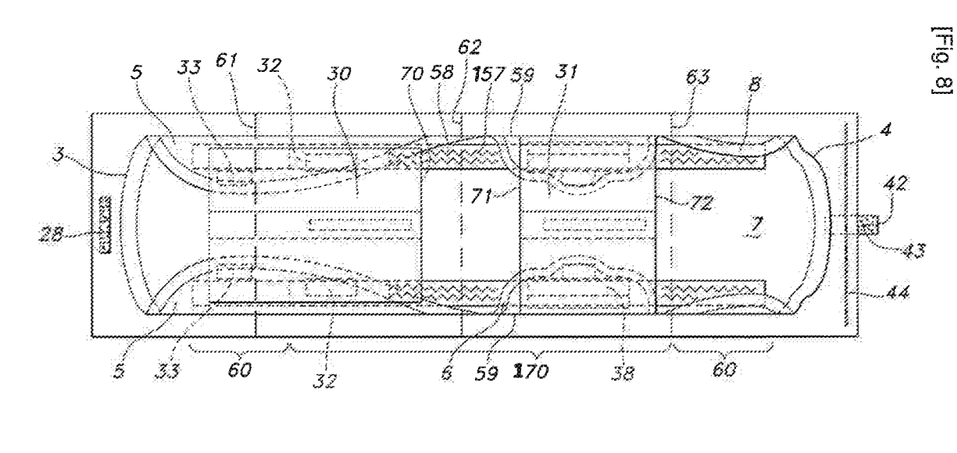
FIG. 8 is a top plan view of an alternative embodiment of an individual article and pouch combination/package of the invention, including an absorbent article containing elastic edge components in a partially opened state.

As can be seen in FIG. 8, which illustrates a top plan view of an alternative embodiment of an individually packaged absorbent article of the invention, an absorbent article in this embodiment includes elastic side features 157 in the form of parallel elastic strands 58 that are positioned along the longitudinal side edges 59 of the article. The elastic strands 58 are tacked down by construction adhesive in end regions 60 such that they are deadened and not elastic in these regions, and do not rise in a wall configuration above the surface of the topsheet when the article is opened. The active elastic strands do cause the elastic side features 157 to rise above the topsheet surface in the region between the two tacked down areas where a wall or barrier is created along the longitudinal side edges 59 of the article. It has been found that by positioning tackdown regions along the first fold line 61 of the article, thereby having the elastic raised wall region 170 begin in the longitudinal direction of the article either, between the rearwardly positioned wing adhesive patches 32, 33 or forward of the rear wing adhesive patches entirely, towards the article forward end 4, and having the remaining fold lines 62, and 63 positioned in regions of the article outside of the regions of the wing adhesive release sheets, elastic performance of the elastic components is preserved. Essentially, in one embodiment, it is desirable for the second fold line 62 to be situated between the front edges 70 of the rearwardly positioned wing release sheets 30 and the rear edges 71 of the forwardly positioned wing release sheets 31, and for the third fold line 63 to be positioned between the front edges 72 of the forwardly positioned wing release sheets 31 and the article forward edge 4.

While the invention has been described in detail with respect to the specific embodiments thereof, it will be appreciated that those skilled in the art, upon attaining an understanding of the foregoing, may readily conceive of alterations to, and variations to these embodiments. Accordingly, the scope of the present invention should be assessed as that of the appended claims.

The invention claimed is:

1. An individually packaged absorbent article comprising: (a) an absorbent article extending in a longitudinal direction and comprising a main body portion having a pair of longitudinal side edges, a pair of end edges, including a forward end edge and a rearward end edge, a garment facing surface provided with a main body garment fastener and a main body garment fastener cover, and a body facing surface, wherein the garment facing surface of the main body portion may be placed in a wearer's undergarment, and the absorbent article comprises a pair of forwardly positioned wings joined to the main body portion and extending laterally outward beyond the longitudinal side edges of the main body portion, wherein a garment facing surface of each of the forwardly positioned wings comprises a forwardly positioned wing fastener, and the forwardly positioned wings are folded over the body facing surface of the main body portion to expose the forwardly positioned wing fasteners, said main body portion further including a pair of rearwardly positioned wings joined to the main body portion at a position closer to the rearward end edge than said forwardly positioned pair of wings, and extending laterally outward beyond the longitudinal side edges of the main body portion, wherein a garment facing surface of each of the rearwardly positioned pair of wings comprises at least two rearwardly positioned wing fasteners wherein the rearwardly positioned wing fasteners of each rearwardly positioned wing are positioned adjacent to each other in the article longitudinal direction, and the rearwardly positioned pair of wings are folded over the body facing surface of the main body portion to expose the rearwardly positioned wing fasteners, (b) a wrapper for the absorbent article, the wrapper comprising a main wrapper sheet, a pair of forwardly positioned wing fastener covers, and a pair of rearwardly positioned wing fastener covers, wherein the main wrapper sheet comprises a pair of longitudinal side portions, a pair of end portions, an article facing surface and an outer surface, (c) wherein the main wrapper sheet comprises at least three fold lines and four faces divided by the three fold lines, wherein the four faces each include an article-oriented face and an article opposing face, wherein the four faces comprise a first face onto which the article rearward end edge extends, a second face onto which at least a portion of the folded rearwardly positioned wings and one or more of the rearwardly positioned wing fasteners are situated, a third face onto which the folded forwardly positioned wings are situated, and a fourth face onto which the forward end edge of the article is situated, wherein the fold lines comprise a first fold line extending between the first face and the second face, the second fold line extending between the second face and the third face, and the third fold line extending between the third face and the fourth face, (d) the pair of forwardly positioned wing fastener covers releasably adhered to each other, with each of the pair of forwardly positioned wing fastener covers comprising a pair of longitudinal side portions, a pair of end portions, a releasable surface facing the wing fasteners of the forwardly positioned wings, and an opposing surface, wherein the pair of forwardly positioned wing fastener covers extend only on the third face between the second and third fold lines, and the pair of forwardly positioned wing fastener covers are releasably affixed to the wing fasteners of the forwardly positioned wings, wherein, (e) the pair of rearwardly positioned wing fastener covers releasably adhered to each other, with each of the pair of rearwardly positioned wing fastener covers comprising a pair of longitudinal side portions, a pair of end portions, a releasable surface facing the pair of rearwardly positioned wing fasteners of the rearwardly positioned wings, and an opposing surface, wherein the pair of rearwardly positioned wing fastener covers extend at least on the second face between the first and second fold lines, and the pair of rearwardly positioned wing fastener covers are releasably affixed to the pair of rearwardly positioned wing fasteners of the pair of rearwardly positioned wings, wherein (f) the main wrapper sheet includes a first wing catch patch on the article-oriented face of the first face, for connecting to said pair of rearwardly positioned wing fastener covers when said article is in a folded configuration, and said main wrapper sheet further includes a second wing catch patch on the article-opposing face of the first face, for connecting to said forwardly positioned wing fastener covers when said article is in a folded configuration, (g) the main wrapper sheet and the main body portion of the absorbent article are folded as a unit about the first, second and third fold lines so that the rearwardly positioned wing fastener covers are superposed with the first wing catch patch and the forwardly positioned wing fastener covers are superposed with the second wing catch patch, and all fastener covers are removed with the wrapper in one or more steps upon removal of the article from the wrapper, wherein said absorbent article further includes elastic side features, wherein said elastic side features form an elastic raised wall region that begins forward of the at least two rearwardly positioned wing fasteners of each rearwardly positioned wing.

2. The individually packaged absorbent article of claim 1, wherein the main body garment fastener cover is adhered to the wrapper.

3. The individually packaged absorbent article of claim 1, wherein the rearwardly positioned wing fasteners of each rearwardly positioned wing are situated on each side of the first fold line.

4. The individually packaged absorbent article of claim 1, wherein the rearwardly positioned wing fastener covers ale positioned solely on the second face.

5. The individually packaged absorbent article of claim 1, wherein said first fold line is situated between two rearwardly positioned wing fasteners.

6. The individually packaged absorbent article of claim 1, wherein said rearwardly positioned wing fasteners are situated entirely forward of said first fold line.

7. The individually packaged absorbent article of claim 1, wherein at least said second and third fold lines are situated over regions of said article not including wing fastener covers.

8. The individually packaged absorbent article of claim 7, wherein said first, second, and third fold lines are situated over regions of said article not including wing fastener covers.

9. The individually packaged absorbent article of claim 1, wherein said wing catch patches are selected from the fastener group of a hot melt adhesive, a pressure sensitive adhesive and a mechanical fastener.

10. The individually packaged absorbent article of claim 1, wherein said rearwardly positioned wing fastener covers extend between both the first and second wrapper faces.

11. The individually packaged absorbent article of claim 1, wherein said elastic side features are deadened in a region of said rearwardly positioned wing fasteners.

12. An individually packaged absorbent article comprising: (a) an absorbent article extending in a longitudinal direction and comprising a main body portion having a pair of longitudinal side edges, a pair of end edges, including a forward end edge and a rearward end edge, a garment facing surface provided with a main body garment fastener and a main body garment fastener cover, and a body facing surface, wherein the garment facing surface of the main body portion may be placed in a wearer's undergarment, and the absorbent article comprises a pair of forwardly positioned wings joined to the main body portion and extending laterally outward beyond the longitudinal side edges of the main body portion, wherein a garment facing surface of each of the forwardly positioned wings comprises a forwardly positioned wing fastener, and the forwardly positioned wings are folded over the body facing surface of the main body portion to expose the forwardly positioned wing fasteners, said main body portion further including a pair of rearwardly positioned wings joined to the main body portion at a position closer to the rearward end edge than said forwardly positioned pair of wings, and extending laterally outward beyond the longitudinal side edges of the main body portion, wherein a garment facing surface of each of the rearwardly positioned pair of wings comprises at least two rearwardly positioned wing fasteners wherein the rearwardly positioned wing fasteners of each rearwardly positioned wing are positioned adjacent to each other in the article longitudinal direction, and the rearwardly positioned pair of wings are folded over the body facing surface of the main body portion to expose the rearwardly positioned wing fasteners, (b) a wrapper for the absorbent article, the wrapper comprising a main wrapper sheet, a forwardly positioned wing fastener cover, and a rearwardly positioned wing fastener cover, wherein the main wrapper sheet comprises a pair of longitudinal side portions, a pair of end portions, an article facing surface and an outer surface, (c) wherein the main wrapper sheet comprises at least three fold lines and four faces divided by the three fold lines, wherein the four faces each include an article-oriented face and an article opposing face, wherein the four faces comprise a first face onto which the article rearward end edge extends, a second face onto which at least a portion of the folded rearwardly positioned wings and one or more of the rearwardly positioned wing fasteners are situated, a third face onto which the folded forwardly positioned wings are situated, and a fourth face onto which the forward end edge of the article is situated, wherein the fold lines comprise a first fold line extending between the first face and the second face, the second fold line extending between the second face and the third face, and the third fold line extending between the third face and the fourth face, (d) the forwardly positioned wing fastener cover comprising a pair of longitudinal side portions, a pair of end portions, a releasable surface facing the wing fasteners of the forwardly positioned wings, and an opposing surface, wherein the forwardly positioned wing fastener cover extends only on the third face between the second and third fold lines, and the forwardly positioned wing fastener cover is releasably affixed to the wing fasteners of the forwardly positioned wings, wherein, (e) the rearwardly positioned wing fastener cover comprising a pair of longitudinal side portions, a pair of end portions, a releasable surface facing the pair of rearwardly positioned wing fasteners of the rearwardly positioned wings, and an opposing surface, wherein the rearwardly positioned wing fastener cover extends at least on the second face between the first and second fold lines, and the rearwardly positioned wing fastener cover is releasably affixed to the pair of rearwardly positioned wing fasteners of the pair of rearwardly positioned wings, wherein (f) the main wrapper sheet includes a first wing catch patch on the article-oriented face of the first face, for connecting to said rearwardly positioned wing fastener cover when said article is in a folded configuration, and said main wrapper sheet further includes a second wing catch patch on the article-opposing face of the first face, for connecting to said forwardly positioned wing fastener cover when said article is in a folded configuration, (g) the main wrapper sheet and the main body portion of the absorbent article are folded as a unit about the first, second and third fold lines so that the rearwardly positioned wing fastener cover is superposed with the first wing catch patch and the forwardly positioned wing fastener cover is superposed with the second wing catch patch, and all fastener covers are removed with the wrapper in one or more steps upon removal of the article from the wrapper, wherein said absorbent article further includes elastic side features, wherein said elastic side features form an elastic raised wall region that begins forward of the at least two rearwardly positioned wing fasteners of each rearwardly positioned wing.

13. The individually packaged absorbent article of claim 12, wherein the main body garment fastener cover is adhered to the wrapper.

14. The individually packaged absorbent article of claim 12, wherein the rearwardly positioned wing fasteners of each rearwardly positioned wing are situated on each side of the first fold line.

15. The individually packaged absorbent article of claim 12, wherein the rearwardly positioned wing fastener covers are positioned solely on the second face.

16. The individually packaged absorbent article of claim 12, wherein said first fold line is situated between two rearwardly positioned wing fasteners.

17. The individually packaged absorbent article of claim 12, wherein said rearwardly positioned wing fasteners are situated entirely forward of said first fold line.

18. The individually packaged absorbent article of claim 12, wherein at least said second and third fold lines are situated over regions of said article not including wing fastener covers.

19. The individually packaged absorbent article of claim 18, wherein said first, second, and third fold lines are situated over regions of said article not including wing fastener covers.

20. The individually packaged absorbent article of claim 12, wherein said wing catch patches are selected from the fastener group of a hot melt adhesive, a pressure sensitive adhesive and a mechanical fastener.

21. The individually packaged absorbent article of claim 12, wherein said rearwardly positioned wing fastener covers extend between both the first and second wrapper faces.

22. The individually packaged absorbent article of claim 12, wherein said elastic side features are deadened in a region of said rearwardly positioned wing fasteners.

23. An individually packaged absorbent article comprising: (a) an absorbent article extending in a longitudinal direction and comprising a main body portion having a pair of longitudinal side edges, a pair of end edges, including a forward end edge and a rearward end edge, a garment facing surface provided with a main body garment fastener, and a body facing surface, wherein the garment facing surface of the main body portion may be placed in a wearer's undergarment, and the absorbent article comprises a pair of forwardly positioned wings joined to the main body portion and extending laterally outward beyond the longitudinal side edges of the main body portion, wherein a garment facing surface of each of the forwardly positioned wings comprises a forwardly positioned wing fastener, and the forwardly positioned wings are folded over the body facing surface of the main body portion to expose the forwardly positioned wing fasteners, said main body portion further including a pair of rearwardly positioned wings joined to the main body portion at a position closer to the rearward end edge than said forwardly positioned pair of wings, and extending laterally outward beyond the longitudinal side edges of the main body portion, wherein a garment facing surface of each of the rearwardly positioned pair of wings comprises at least two rearwardly positioned wing fasteners wherein the rearwardly positioned wing fasteners of each rearwardly positioned wing are positioned adjacent to each other in the article longitudinal direction, and the rearwardly positioned pair of wings are folded over the body facing surface of the main body portion to expose the rearwardly positioned wing fasteners, (b) a wrapper for the absorbent article, the wrapper comprising a main wrapper sheet, a main body garment fastener cover adhered thereto, a pair of forwardly positioned wing fastener covers, and a pair of rearwardly positioned wing fastener covers, wherein the main wrapper sheet comprises a pair of longitudinal side portions, a pair of end portions, an article facing surface and an outer surface, (c) wherein the main wrapper sheet comprises at least three fold lines and four faces divided by the three fold lines, wherein the four faces each include an article-oriented face and an article opposing face, wherein the four faces comprise a first face onto which the article rearward end edge extends, a second face onto which at least a portion of the folded rearwardly positioned wings and one or more of the rearwardly positioned wing fasteners are situated, a third face onto which the folded forwardly positioned wings are situated, and a fourth face onto which the forward end edge of the article is situated, wherein the fold lines comprise a first fold line extending between the first face and the second face, the second fold line extending between the second face and the third face, and the third fold line extending between the third face and the fourth face, (d) the pair of forwardly positioned wing fastener covers releasably adhered to each other, with each of the pair of forwardly positioned wing fastener covers comprising a pair of longitudinal side portions, a pair of end portions, a releasable surface facing the wing fasteners of the forwardly positioned wings, and an opposing surface, wherein the pair of forwardly positioned wing fastener covers extend only on the third face between the second and third fold lines, and the pair of forwardly positioned wing fastener covers are releasably affixed to the wing fasteners of the forwardly positioned wings, wherein, (e) the pair of rearwardly positioned wing fastener covers releasably adhered to each other, with each of the pair of rearwardly positioned wing fastener covers comprising a pair of longitudinal side portions, a pair of end portions, a releasable surface facing the pair of rearwardly positioned wing fasteners of the rearwardly positioned wings, and an opposing surface, wherein the pair of rearwardly positioned wing fastener covers extend at least on the second face between the first and second fold lines, and the pair of rearwardly positioned wing fastener covers are releasably affixed to the pair of rearwardly positioned wing fasteners of the pair of rearwardly positioned wings, wherein (f) the main wrapper sheet includes a first wing catch patch on the article-oriented face of the first face, for connecting to said pair of rearwardly positioned wing fastener covers when said article is in a folded configuration, and said main wrapper sheet further includes a second wing catch patch on the article-opposing face of the first face, for connecting to said forwardly positioned wing fastener covers when said article is in a folded configuration, (g) the main wrapper sheet and the main body portion of the absorbent article are folded as a unit about the first, second and third fold lines so that the rearwardly positioned wing fastener covers are superposed with the first wing catch patch and the forwardly positioned wing fastener covers are superposed with the second wing catch patch, and all fastener covers are removed with the wrapper in one step upon removal of the article from the wrapper, wherein said absorbent article further includes elastic side features, wherein said elastic side features form an elastic raised wall region that begins forward of the at least two rearwardly positioned wing fasteners of each rearwardly positioned wing.

\* \* \* \* \*